US010196625B2

(12) United States Patent
Takatsu et al.

(10) Patent No.: US 10,196,625 B2
(45) Date of Patent: Feb. 5, 2019

(54) METHOD FOR IMPROVING BLOOD PERSISTENCE OF PROTEIN

(71) Applicant: SEIKAGAKU CORPORATION, Tokyo (JP)

(72) Inventors: Yoshihiro Takatsu, Tokyo (JP); Masanobu Fukushima, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 0 days.

(21) Appl. No.: 15/025,606

(22) PCT Filed: Sep. 30, 2014

(86) PCT No.: PCT/JP2014/076194
§ 371 (c)(1),
(2) Date: Mar. 29, 2016

(87) PCT Pub. No.: WO2015/046602
PCT Pub. Date: Apr. 2, 2015

(65) Prior Publication Data
US 2016/0235857 A1  Aug. 18, 2016

(30) Foreign Application Priority Data

Sep. 30, 2013 (JP) ................................ 2013-204053

(51) Int. Cl.
| | | |
|---|---|---|
| *C12N 9/96* | (2006.01) | |
| *A61K 47/61* | (2017.01) | |
| *C12N 9/82* | (2006.01) | |
| *A61K 38/21* | (2006.01) | |
| *A61K 38/27* | (2006.01) | |
| *A61K 38/38* | (2006.01) | |
| *A61K 38/50* | (2006.01) | |

(52) U.S. Cl.
CPC .............. *C12N 9/82* (2013.01); *A61K 38/212* (2013.01); *A61K 38/27* (2013.01); *A61K 38/38* (2013.01); *A61K 38/50* (2013.01); *A61K 47/61* (2017.08); *C12N 9/96* (2013.01); *C12Y 305/01001* (2013.01); *Y02A 50/473* (2018.01)

(58) Field of Classification Search
None
See application file for complete search history.

(56) References Cited

U.S. PATENT DOCUMENTS

| 4,585,754 A * | 4/1986 | Meisner ............... A61K 38/446 |
|---|---|---|
| | | 424/94.4 |
| 5,310,881 A | 5/1994 | Sakurai et al. |
| 6,562,781 B1 | 5/2003 | Berry et al. |
| 2003/0100487 A1* | 5/2003 | Berry et al. |
| 2003/0104601 A1 | 6/2003 | DeAngelis |
| 2003/0109693 A1 | 6/2003 | Ninomiya et al. |
| 2009/0263867 A1 | 10/2009 | Sugiura et al. |
| 2010/0151532 A1 | 6/2010 | Suzuki et al. |
| 2011/0244520 A1* | 10/2011 | Doherty et al. |

FOREIGN PATENT DOCUMENTS

| EP | 0 445 304 A1 | 9/1991 |
|---|---|---|
| JP | 62255435 A | 11/1987 |
| JP | 03284698 A | 12/1991 |
| JP | 5-39306 A | 2/1993 |
| JP | 2002-338599 A | 11/2002 |
| JP | 4101548 B2 | 6/2008 |
| JP | 2008-295450 A | 12/2008 |
| JP | 2013520995 A | 6/2013 |
| WO | 91/04276 A1 | 4/1991 |

OTHER PUBLICATIONS

Chiara Schiraldi et al., "Production of chondroitin sulfate and chondroitin", Appl Microbial Biotechnol, 2010, pp. 1209-1220, vol. 87.
International Search Report for PCT/JP2014/076194 dated Dec. 9, 2014.
EESR issued in the corresponding European application No. 14848402.5 dated May 15, 2017.
Volpi, "Milligram-scale preparation and purification of oligosaccharides of defined length possessing the structure of chondroitin from defructosylated capsular polysaccharide K4", Glycobiology, vol. 13, No. 9, 2003, pp. 635-640.
International Preliminary Report on Patentability dated Apr. 14, 2016 from the International Bureau in international application No. PCT/JP2014/076194.

* cited by examiner

*Primary Examiner* — Kade Ariani
(74) *Attorney, Agent, or Firm* — Sughrue Mion, PLLC (57) ABSTRACT

Provided herein is a means for increasing protein retention in blood. The protein retention in blood is increased by forming a conjugate of a protein and chondroitin produced by a microorganism having chondroitin-producing capability and/or chondroitin synthesized with a chondroitin synthase.

2 Claims, 3 Drawing Sheets

METHOD FOR IMPROVING BLOOD PERSISTENCE OF PROTEIN

CROSS REFERENCE TO RELATED APPLICATIONS

This application is a National Stage of International Application No. PCT/JP2014/076194 filed Sep. 30, 2014, claiming priority based on Japanese Patent Application No. 2013-204053 filed Sep. 30, 2013, the contents of all of which are incorporated herein by reference in their entirety.

TECHNICAL FIELD

The present invention relates to a technique for increasing protein retention in blood.

BACKGROUND ART

Chondroitin, a type of glycosaminoglycan, is a glycan (sugar chain) having a basic backbone of a repeating disaccharide structure [→4)-β-GlcUA-(1→3)-β-GalNAc-(1→] consisting of glucuronic acid (GlcUA) and N-acetylgalactosamine (GalNAc). In the body of animals, chondroitin typically occurs as chondroitin sulfate that is sulfated at some of the hydroxyl groups of the constituent sugars. For example, chondroitin that is sulfated at the hydroxyl group in position 4 of the GalNAc residues (chondroitin-4-sulfate) is called chondroitin sulfate A, and chondroitin that is sulfated at the hydroxyl group in position 6 of the GalNAc residues (chondroitin-6-sulfate) is called chondroitin sulfate C.

Patent Document 1 describes a protein having covalently linked chondroitin. The document also describes that the protein has improved stability against degradation in vivo compared to unmodified one. However, in the document, the term "chondroitin" is intended to mean "chondroitin sulfate", such as chondroitin-4-sulfate and chondroitin-6-sulfate (see the top left column in page 4 of the document).

Patent Document 2 describes a physiologically active human thrombomodulin polypeptide, which is an isolated polypeptide having a glycan comprising chondroitin and/or chondroitin sulfate in the peptide chain (type-II thrombomodulin polypeptide). The document also describes that the polypeptide has higher activity than a polypeptide substantially having no glycan comprising chondroitin and/or chondroitin sulfate (type-I thrombomodulin polypeptide).

Patent Document 3 describes a protein modified with a glycosaminoglycan. The document also describes that the protein is more stable in vivo and capable of more sustainably developing physiological activity, than unmodified one. Moreover, Patent Document 4 describes a covalent conjugate comprising of a glycosaminoglycan linked to a protein by a covalent linkage. The document also describes that pharmacokinetic properties are improved by conjugation of a glycosaminoglycan. Though Patent Documents 3 and 4 refer to chondroitin, chondroitin is merely exemplified as a material that falls in the same category as many other glycosaminoglycans (i.e. colominic acid, hyaluronic acid, chondroitin sulfate, teichuronic acid, dermatan sulfate, heparin, heparan sulfate, keratan sulfate, keratan polysulfate, and derivatives thereof). In fact, these documents do not disclose or suggest whether or not protein stability depends on the type of glycosaminoglycan conjugated to the protein.

Furthermore, the foregoing documents do not disclose or suggest using chondroitin produced by a microorganism having chondroitin-producing capability or chondroitin synthesized with a chondroitin synthase.

In nature, chondroitin is to be present in nematodes, eye cornea of cow, skin of Japanese flying squid (*Todarodes pacificus*) and common octopus (*Octopus vulgaris*), and the like. However, since natural chondroitin are scarce, it is impractical to produce chondroitin from these sources in industrial scale. Accordingly, chondroitin is typically produced by desulfation of chondroitin sulfate, and such chondroitin is generally used as chondroitin.

In recent years, there have been reports of chondroitin production by using a microorganism. Patent Documents 5 to 7 describe bacteria of *Escherichia* having chondroitin-producing capability and chondroitin produced by the bacteria. Patent Documents 8 and 9 disclose methods for synthesizing chondroitin in vitro with a chondroitin synthase. However, these documents do not disclose or suggest using chondroitin produced by microorganisms such as bacteria or chondroitin synthesized with a chondroitin synthase for increasing protein retention in blood.

Moreover, Patent Documents 1 to 9 do not disclose or suggest that retention of a glycosaminoglycan itself in blood varies with the type or the origin of the glycosaminoglycan. These documents also do not disclose or suggest that chondroitin produced by a microorganism or chondroitin synthesized with an enzyme have much longer retention in blood than other glycosaminoglycans. Furthermore, Patent Documents 1 to 9 do not disclose or suggest that a complex consisting of a protein conjugated with chondroitin produced by a microorganism or chondroitin synthesized with an enzyme have much longer retention in blood than a complex consisting of a protein conjugated with chondroitin obtained through desulfation of chondroitin sulfate or other glycosaminoglycans.

PRIOR ART DOCUMENTS

Patent Documents

Patent Document 1: JP-A-62-255435
Patent Document 2: WO1991/4276
Patent Document 3: JP-A-3-284698
Patent Document 4: JP-T-2000-501082
Patent Document 5: JP-A-2008-295450
Patent Document 6: JP-T-2010-524431
Patent Document 7: JP-T-2013-520995
Patent Document 8: Japanese Patent No. 4101548
Patent Document 9: Japanese Patent No. 5081629

SUMMARY OF THE INVENTION

Problems to be Solved by the Invention

An object of the present invention is to provide a technique for increasing protein retention in blood.

Means for Solving the Problems

The present inventors found that chondroitin produced by a microorganism having chondroitin-producing capability have much longer retention in blood than other glycosaminoglycans. Moreover, the present inventors also found that chondroitin produced by a microorganism having a chondroitin-producing capability can greatly increase protein retention in blood by means of forming a conjugate of the protein and it, compared to the case of conjugating the other glycosaminoglycans to the protein. Furthermore, surprisingly, the present inventors also found that chondroitin produced by a microorganism having chondroitin-producing capability can greatly increase protein retention in blood by means of forming a conjugate of the protein and it, compared to chondroitin produced by desulfation of chondroitin sulfate. The present invention has been accomplished on the basis of these findings.

Accordingly, the foregoing object can be solved by the following examples of the present invention.

An agent for increasing protein retention in blood, the agent containing, as an active ingredient, chondroitin produced by a microorganism having chondroitin-producing capability and/or chondroitin synthesized with a chondroitin synthase.

The agent, wherein the microorganism is a bacterium.

The agent, wherein the bacterium is a bacterium of *Escherichia*.

The agent, wherein the bacterium is *Escherichia coli*.

The agent, wherein the chondroitin synthase is a chondroitin polymerase.

The agent, wherein the chondroitin is chondroitin that does not have a side chain.

A conjugate of a protein and chondroitin produced by a microorganism having chondroitin-producing capability and/or chondroitin synthesized with a chondroitin synthase.

The conjugate, wherein the conjugate is formed by a covalent bond between the protein and the chondroitin.

A pharmaceutical composition containing the conjugate.

A protein preparation having increased retention in blood, the protein preparation containing the conjugate.

A method for increasing protein retention in blood, the method comprising the step of forming a conjugate of a protein and chondroitin produced by a microorganism having chondroitin-producing capability and/or chondroitin synthesized with a chondroitin synthase.

A method for producing a protein having increased retention in blood, the method comprising the step of forming a conjugate of a protein and chondroitin produced by a microorganism having chondroitin-producing capability and/or chondroitin synthesized with a chondroitin synthase.

The method, wherein the conjugate is formed by a covalent bond.

MODES FOR CARRYING OUT THE INVENTION

[1] Chondroitin for use in the Present Invention

The chondroitin for use in the present invention (hereinafter, also referred to as "chondroitin of the present invention") is chondroitin produced by a microorganism having chondroitin-producing capability and/or chondroitin synthesized with a chondroitin synthase. Hereafter, chondroitin produced by a microorganism having chondroitin-producing capability is also referred to as "microorganism-derived chondroitin". Moreover, hereafter, chondroitin synthesized with a chondroitin synthase is also referred to as "enzymatically synthesized chondroitin". Specifically, the "microorganism-derived chondroitin" is, for example, chondroitin produced by culturing microorganisms having chondroitin-producing capability. Moreover, specifically, the "enzymatically synthesized chondroitin" is, for example, chondroitin synthesized with a chondroitin synthase either in vitro or in a cell-free system.

As used herein, "chondroitin" refers to a glycan (sugar chain) having a basic backbone of a repeating disaccharide structure [→4)-β-GlcUA-(1→3)-β-GalNAc-(1→] consisting of glucuronic acid (GlcUA) and N-acetylgalactosamine (GalNAc). The basic backbone is also referred to as "chondroitin backbone". The chondroitin may have or may not have a side chain. Accordingly, specifically, the chondroitin may be a glycan having a side chain on its chondroitin backbone (hereinafter, also referred to as "chondroitin having a side chain"), or a glycan that does not have a side chain on its chondroitin backbone (hereinafter, also referred to as "chondroitin having no side chain"). Examples of the side chain include sugar residues such as fructose (Fru). Examples of the chondroitin having a side chain include K4 polysaccharide (fructosylated chondroitin), which is a glycan formed by repeated polymerization of a trisaccharide structure consisting of GalNAc, GlcUA and Fru. Examples of the K4 polysaccharide include a polysaccharide produced by K4 strain of *Escherichia coli*. Examples of the chondroitin having no side chain include chondroitin that inherently does not have a side chain (chondroitin produced in a form of lacking a side chain) and chondroitin from which the side chain has been removed. Examples of the chondroitin from which the side chain has been removed include K4 polysaccharide from which fructose residues has been removed (defructosylated K4 polysaccharide). The side chain can be removed by, for example, acid hydrolysis reaction (Lidholt K, Fjelstad M., J Biol Chem. 1997 Jan. 31; 272(5): 2682-7). The "chondroitin having no side chain" is not limited to chondroitin that does not have any side chain, but also includes chondroitin that substantially does not have side chains. As used herein, the "chondroitin that substantially does not have side chains" refers to chondroitin in which the proportion of the number of sugar residues having a side chain is 5% or less of the number of the all sugar residues forming the chondroitin backbone, and may refer to chondroitin in which the proportion of the number of sugar residues having a side chain is 3% or less, 1% or less, or 0.5% or less of the number of the all sugar residues forming the chondroitin backbone.

Preferably, the chondroitin is chondroitin having no side chain. Accordingly, in an embodiment of the present invention, the "chondroitin" may exclude chondroitin having a side chain, such as K4 polysaccharide. Moreover, preferably, the chondroitin is chondroitin that inherently does not have a side chain. Accordingly, in an embodiment of the present invention, "chondroitin" may exclude chondroitin from which the side chain has been removed, such as defructosylated K4 polysaccharide.

In the present invention, "chondroitin" excludes chondroitin sulfate. Moreover, the "chondroitin of the present invention" excludes chondroitin obtained through desulfation of chondroitin sulfate.

The molecular weight of the chondroitin of the present invention is not particularly limited, as long as the chondroitin of the present invention can increase protein retention in blood by forming a conjugate with the protein. The chondroitin of the present invention may have a molecular weight of, for example, $6 \times 10^2$ to $1 \times 10^6$, $3 \times 10^3$ to $1 \times 10^6$, $3 \times 10^3$ to $1 \times 10^6$, or $3 \times 10^3$ to $5 \times 10^4$ in terms of a weight-average molecular weight. Moreover, the chondroitin of the present invention may have a molecular weight of, for example, $1 \times 10^4$ or more in terms of a weight-average molecular weight. As used herein, the "weight-average molecular weight" is a weight-average molecular weight as measured by gel filtration chromatography.

<Microorganism-Derived Chondroitin>

The "microorganism having chondroitin-producing capability" refers to a microorganism having the capability to produce the chondroitin of the present invention. The "capability to produce the chondroitin of the present invention" may be, for example, capability to produce the chondroitin of the present invention itself or capability to produce modified chondroitin. The "modified chondroitin" refers to a glycan that has chondroitin backbone and is usable as a material to produce the chondroitin of the present invention. The "modified chondroitin" may be, for example, a glycan consisting of the chondroitin of the present invention and other sugars attached thereto. Specifically, the "modified chondroitin" may be, for example, chondroitin having a side chain when the chondroitin of the present invention is chondroitin from which the side chain has been removed. For example, when K4 polysaccharide is produced by a microorganism, the K4 polysaccharide may be used as the chondroitin of the present invention, either directly or preferably after being defructosylated. Accordingly, a microorganism having K4 polysaccharide-producing capability may be included in the "microorganism having chondroitin-producing capability". Moreover, both K4 polysaccharide produced by a microorganism and defructosylated K4 polysaccharide obtained by defructosylating such K4 polysaccharide may be included in the "microorganism-derived chondroitin".

Preferably, the "capability to produce the chondroitin of the present invention" is capability to produce the chondroitin of the present invention itself. Accordingly, in an embodiment of the present invention, the "microorganism having chondroitin-producing capability" may exclude a microorganism that produces modified chondroitin. Specifically, for example, in the present invention, "microorganism having chondroitin-producing capability" may exclude a microorganism that produces a glycan consisting of the chondroitin of the present invention and other sugars attached thereto, because the chondroitin of the present invention cannot be obtained unless the other sugars are removed from the produced glycan. More specifically, for example, "microorganism having chondroitin-producing capability" may exclude a microorganism that produces chondroitin having a side chain, such as K4 polysaccharide.

The microorganism having chondroitin-producing capability may be, for example, a microorganism that produces chondroitin inside the cell, a microorganism that produces chondroitin into a medium, or a microorganism that produces chondroitin on the bacterial cell surface layer (for example, on the cell membrane or on the cell wall). Examples of the microorganism that produce chondroitin on the bacterial cell surface layer include a microorganism that produces chondroitin as a capsular polysaccharide.

The type of a microorganism is not particularly limited. Examples of the microorganisms include bacteria and yeast. The microorganisms are preferably bacteria, for considerations such as productivity of chondroitin and ease of handling.

The type of bacteria is not particularly limited. Examples of the bacteria include bacteria of *Gluconacetobacter*, such as *Gluconacetobacter hansenii* and *Gluconacetobacter xylinus*; bacteria of *Rhizobium*, such as *Rhizobium meffloti*; bacteria of *Acetobacter*, such as *Acetobacter xylinum*; bacteria of *Erwinia*, such as *Erwinia amylovora*; bacteria of *Thiobacillus*, such as *Thiobacillus ferrooxidans*; bacteria of *Xylella*, such as *Xylella fastidiosa*; bacteria of *Sinorhizobium*, such as *Sinorhizobium meliloti*; bacteria of *Rhodococcus*, such as *Rhodococcus rhodochrous*; bacteria of *Klebsiella*, such as *Klebsiella aerogenes*; bacteria of *Enterobacter*, such as *Enterobacter aerogenes*; and bacteria of *Escherichia*, such as *Escherichia coli*, as disclosed in Patent Document 6. Other examples of the bacteria include non-pathogenic organisms, such as bacteria of *Pseudomonas*, bacteria of *Xanthomonas*, bacteria of *Methylomonas*, bacteria of *Acinetobacter*, and bacteria of *Sphingomonas*, as disclosed in Patent Document 7. Moreover, other examples of the bacteria include *Pasteurella multocida*.

The bacteria are preferably bacteria of *Escherichia*, for considerations such as productivity of chondroitin, versatility, and ease of handling. Particularly preferred are *Escherichia coli*, which are especially versatile, and easy to handle. Examples of *Escherichia coli* include *Escherichia coli* K-12 strain, such as W3110 strain (ATCC 27325) and MG1655 strain (ATCC 47076); *Escherichia coli* K4 strain, such as NCDC U1-41 strain (ATCC 23502); *Escherichia coli* K5 strain, such as NCDC Bi 8337-41 strain (ATCC 23506); *Escherichia coli* B strain, such as BL21 strain; and derived strains thereof. These strains are available from, for example, the catalogs or websites of American Type Culture Collection (ATCC) (P.O. Box 1549 Manassas, Va. 20108, the United States of America), The International *Escherichia* and *Klebsiella* Centre (WHO), and Statens Serum Institut (Building 37K, Room 125c Artillerivej 5 DK-2300 Copenhagen S Denmark).

The microorganism having chondroitin-producing capability may be a microorganism inherently having a capability to produce the chondroitin of the present invention or a microorganism that has been modified to have a capability to produce the chondroitin of the present invention. The microorganism having chondroitin-producing capability may be obtained by, for example, imparting chondroitin-producing capability to such a microorganism as described above.

Examples of the microorganism inherently having a capability to produce the chondroitin of the present invention include *Escherichia coli* K4 strain and *Pasteurella multocida* type F. *Escherichia coli* K4 strain produces chondroitin having fructose residues as side chains (K4 polysaccharide). Accordingly, *Escherichia coli* K4 strain, for example, may be directly used as the "microorganism having chondroitin-producing capability", or may be used as the "microorganism having chondroitin-producing capability" after being modified so that the product chondroitin (K4 polysaccharide) does not have fructose residues as side chains. Such modified strains of *Escherichia coli* K4 strain (strains modified to produce chondroitin (K4 polysaccharide) that does not have fructose residues as side chains) may be obtained by, for example, inactivating the kfoE gene of *Escherichia coli* K4 strain. The kfoE gene of *Escherichia coli* K4 strain may be inactivated using known methods, for example, the method described in JP-T-2013-531995.

The chondroitin-producing capability may be imparted by, for example, expressibly transforming a microorganism with a gene that encodes a protein involved in chondroitin production.

When the chondroitin-producing capability is the capability to produce chondroitin having a side chain, the chondroitin-producing capability may be imparted by, for example, expressibly transforming a microorganism having side chain-attaching capability with a gene that encodes a protein involved in chondroitin production. Here, the "microorganism having side chain-attaching capability" is, for example, a microorganism having a gene that encodes a protein involved in attachment of a side chain. The "microorganism having a gene that encodes a protein involved in attachment of a side chain" may be, for example, a microorganism that inherently has the gene, or a microorganism that is expressibly transformed with the gene.

When the chondroitin-producing capability is the capability to produce chondroitin having no side chain, the chondroitin-producing capability may be imparted by, for example, expressibly transforming a microorganism that does not have side chain-attaching capability with a gene that encodes a protein involved in chondroitin production. Here, the "microorganism that does not have side chain-attaching capability" is, for example, a microorganism that does not have a gene that encodes a protein involved in attachment of a side chain. The "microorganism that does not have a gene that encodes a protein involved in attachment of a side chain" may be a microorganism that inherently lacks the gene, or a microorganism in which the gene has been deleted or inactivated.

Examples of the gene that encodes a protein involved in chondroitin production include kfoA, kfoB, kfoC, kfoF, kfoG, kpsF, kpsE, kpsD, kpsU, kpsC, kpsS, kpsM, kpsT, and pmCS genes. Examples of the kfoA, kfoB, kfoC, kfoF, kfoG, kpsF, kpsE, kpsD, kpsU, kpsC, kpsS, kpsM, and kpsT genes include kfoA, kfoB, kfoC, kfoF, kfoG, kpsF, kpsE, kpsD, kpsU, kpsC, kpsS, kpsM, and kpsT genes derived from *Escherichia coli* K4 strain. Examples of the pmCS gene include a pmCS gene derived from *Pasteurella multocida*. Examples of the gene that encodes a protein involved in attachment of a side chain include kfoD, orf3 (kfoI), kfoE, and orf1 (kfoH) genes. Examples of the kfoD, orf3(kfoI), kfoE, and orf1 (kfoH) genes include kfoD, orf3 (kfoI), kfoE, and orf1 (kfoH) genes derived from *Escherichia coli* K4 strain. The nucleotide sequences of these genes, and the amino acid sequences of proteins encoded by these genes can be obtained from, for example, public databases such as NCBI (http://www.ncbi.nlm.nih.gov/). Introduction of a gene may be achieved by, for example, introducing a vector carrying the gene into a microorganism, or introducing the gene onto a chromosome of a microorganism. A gene may be introduced in only one copy, or in two or more copies. In the present invention, only one gene may be introduced, or two or more genes may be introduced.

The introduced gene may be appropriately selected according to factors such as the type of the microorganism used. For example, *Escherichia coli* K5 strain has capability of producing heparosan, a type of glycosaminoglycan, but does not have capability of producing chondroitin. However, *Escherichia coli* K5 strain can acquire chondroitin-producing capability by introducing the kfoA and kfoC genes. As another example, *Escherichia coli* K-12 strain, which does not have capability of producing chondroitin, can acquire chondroitin-producing capability by introducing the kfo gene group (kfoA, kfoB, kfoC, kfoF, and kfoG) and the kps gene group (kpsF, kpsE, kpsD, kpsU, kpsC, kpsS, kpsM, and kpsT). These strains that acquired chondroitin-producing capability can produce, for example, chondroitin as a capsular polysaccharide. The chondroitin produced as a capsular polysaccharide may be used, for example, directly as the chondroitin of the present invention, or after being treated by contacting with an acid such as hydrochloric acid.

Moreover, the microorganism having chondroitin-producing capability may have been modified to enhance expression of an inherent gene of the microorganism encoding a protein involved in chondroitin production. For example, *Escherichia coli* K4 strain may be transformed with a gene that encodes a protein involved in chondroitin production. As another example, *Escherichia coli* K5 strain may be further transformed with a gene that encodes protein involved in chondroitin production, in addition to the kfoA and kfoC genes. Here, the "inherent gene of the microorganism" may be a gene derived from the microorganism or a gene that is not derived from the microorganism. Specifically, for example, *Escherichia coli* K4 strain may be transformed with a gene derived from *Escherichia coli* K4 strain that encodes a protein involved in chondroitin production, or with a gene derived from organisms other than *Escherichia coli* K4 strain that encodes a protein involved in chondroitin production.

Examples of the microorganism having chondroitin-producing capability include the bacteria having chondroitin-producing capability disclosed in Patent Document 6 or 7.

Preferred examples of the microorganism having chondroitin-producing capability include "*Escherichia coli* transformed with the kfoA and kfoC genes derived from *Escherichia coli* K4 strain" described in Patent Document 6. Moreover, when the chondroitin-producing capability is the capability to produce chondroitin having no side chain, preferred examples of the microorganism having chondroitin-producing capability include "*Escherichia coli* transformed with the kfoA and kfoC genes derived from *Escherichia coli* K4 strain and that does not have 1 to 3 or all of the genes selected from kfoD, orf3 (kfoI), kfoE, and orf1 (kfoH) genes". Preferred examples of such *Escherichia coli* include *Escherichia coli* K5 strain transformed with the kfoA and kfoC genes derived from *Escherichia coli* K4 strain. The kfoA and kfoC genes derived from *Escherichia coli* K4 strain may be introduced by using, for example, the method described in Patent Document 6.

Other preferred examples of the microorganism having chondroitin-producing capability include "*Escherichia coli* transformed with the kfoA, kfoB, kfoC, kfoF, kfoG, kpsF, kpsE, kpsD, kpsU, kpsC, kpsS, kpsM, and kpsT genes derived from *Escherichia coli* K4 strain and the xylS gene derived from *Pseudomonas putida*" described in Patent Document 7. Moreover, when the chondroitin-producing capability is the capability to produce chondroitin having no side chain, preferred examples of the microorganism having chondroitin-producing capability include "*Escherichia coli* transformed with the kfoA, kfoB, kfoC, kfoF, kfoG, kpsF, kpsE, kpsD, kpsU, kpsC, kpsS, kpsM, and kpsT genes derived from *Escherichia coli* K4 strain and the xylS gene derived from *Pseudomonas putida*, and that does not have 1 to 3 or all of the genes selected from kfoD, orf3 (kfoI), kfoE, and orf1 (kfoH) genes". Preferred examples of such *Escherichia coli* include *Escherichia coli* transformed with 4 copies each of the kfoA, kfoB, kfoC, kfoF, and kfoG genes derived from *Escherichia coli* K4 strain, 1 copy each of the kpsF, kpsE, kpsD, kpsU, kpsC, kpsS, kpsM, and kpsT genes derived from *Escherichia coli* K4 strain, and 1 copy of the xylS gene derived from *Pseudomonas putida*. Particularly preferred are *Escherichia coli* K-12 strain transformed with these genes. Preferred examples of *Escherichia coli* K-12 strain include *Escherichia coli* K-12 W3110 strain. A bacterial strain obtained by transforming *Escherichia coli* K-12 W3110 strain with the foregoing genes is disclosed as "MSC702 strain" in Patent Document 7. These genes may be introduced by using, for example, the methods described in Patent Document 7.

Here, the genes used to modify a microorganism for imparting chondroitin-producing capability and the like are not limited to the known genes exemplified above, and may be, for example, variants of these genes, as long as the genes encode proteins that maintain original functions. The gene used to modify a microorganism may be, for example, a gene that has a homology of at least 80%, preferably at least 90%, more preferably at least 95%, further preferably at least 97%, particularly preferably at least 99% to the total nucleotide sequence of a known gene, and that encodes a protein that maintains original function. Moreover, the gene used to modify a microorganism may be, for example, a gene encoding a protein that has a homology of at least 80%, preferably at least 90%, more preferably at least 95%, further preferably at least 97%, particularly preferably at least 99% to the total amino acid sequence of a known protein, and that maintains original function. Furthermore, the term "homology" as used herein may mean "identity". Moreover, the gene used to modify a microorganism may be, for example, a gene encoding a protein that has an amino acid sequence of a known protein with the substitution, deletion, insertion, and/or addition of one or several amino acids which occur together at one location or several disperse locations, and that maintains original function. Here, "one or several" may mean, for example, 1 to 30, preferably 1 to 20, more preferably 1 to 10, further preferably 1 to 5, particularly preferably 1 to 3. The substitution, deletion, insertion, and/or addition of an amino acid are conservative mutations that maintain the normal protein function. The conservative mutation is typically a conservative substitution. The conservative substitution as used herein means the substitution between Phe, Trp, and Tyr when the substitution site is an aromatic amino acid, the substitution between Leu, Ile, and Val when the substitution site is a hydrophobic amino acid, the substitution between Gln and Asn when the substitution site is a polar amino acid, the substitution between Lys, Arg, and His when the substitution site is a basic amino acid, the substitution between Asp and Glu when the substitution site is an acidic amino acid, and the substitution between Ser and Thr when the substitution site is an amino acid with a hydroxyl group. Specific examples of substitutions qualified as conservative substitutions include an Ala to Ser or Thr substitution, an Arg to Gln, His, or Lys substitution, an Asn to Glu, Gln, Lys, His, or Asp substitution, an Asp to Asn, Glu, or Gln substitution, a Cys to Ser or Ala substitution, a Gln to Asn, Glu, Lys, His, Asp, or Arg substitution, a Glu to Gly, Asn, Gln, Lys, or Asp substitution, a Gly to Pro substitution, a His to Asn, Lys, Gln, Arg, or Tyr substitution, an Ile to Leu, Met, Val, or Phe substitution, a Leu to Ile, Met, Val, or Phe substitution, a Lys to Asn, Glu, Gln, His, or Arg substitution, a Met to Ile, Leu, Val, or Phe substitution, a Phe to Trp, Tyr, Met, Ile, or Leu substitution, a Ser to Thr, or Ala substitution, a Thr to Ser, or Ala substitution, a Trp to Phe, or Tyr substitution, a Tyr to His, Phe, or Trp substitution, and a Val to Met, Ile, or Leu substitution. The gene used to modify a microorganism may be one in which any of its codons is substituted with an equivalent codon (a different codon encoding the same amino acid). For example, the gene used to modify a microorganism may have been modified so that it has the optimum codon as may be selected according to the codon usage frequency of the host used (the frequency by which the codon will be used in a nucleic acid encoding a protein expressed by the host).

The "microorganism-derived chondroitin" may be produced by, for example, culturing the above-exemplified microorganisms having chondroitin-producing capability. The culture conditions are not particularly limited, as long as the microorganism having chondroitin-producing capability can grow and produce chondroitin. The microorganism having chondroitin-producing capability may be cultured, for example, under the common conditions used to culture microorganisms such as bacteria and yeasts. For details of culture conditions, see, for example, the culture conditions described in Patent Documents 5 to 7.

After culture, the chondroitin may be isolated and purified from the culture by using known methods. Specifically, for example, the chondroitin can be precipitated by using a solvent such as ethanol and thereby collected. Moreover the chondroitin may be further purified by redissolving and precipitating in a cycle or by using anion exchange or other chromatographic techniques.

<Enzymatically Synthesized Chondroitin>

As used herein, "chondroitin synthase" refers to a protein that catalyzes a reaction of alternately attaching an N-acetylgalactosamine (GalNAc) residue and a glucuronic acid (GlcUA) residue to a non-reducing end of a glycan, and thereby elongating a chondroitin chain. The chondroitin synthase may be a protein that works alone to catalyze both the attachment of a GalNAc residue and the attachment of a GlcUA residue, or a combination of a protein that catalyze the addition of a GalNAc residue and a protein that catalyze the addition of a GlcUA residue. Examples of the chondroitin synthase include a chondroitin polymerase. The chondroitin polymerase works alone to catalyze both the attachment of a GalNAc residue and the attachment of a GlcUA residue. Examples of the chondroitin polymerase include the KfoC protein encoded by the kfoC gene, and the PmCS protein encoded by the pmCS gene. Examples of the kfoC gene include the kfoC gene derived from *Escherichia coli* K4 strain. Examples of the pmCS gene include the pmCS gene derived from *Pasteurella multocida*. Preferred examples of the chondroitin synthase include a chondroitin synthase derived from a microorganism. Preferred examples of the chondroitin synthase derived from a microorganism include, specifically, chondroitin synthases that are inherently present in a microorganism, such as the KfoC protein (K4CP) encoded by the kfoC gene derived from *Escherichia coli* K4 strain, and the PmCS protein encoded by the pmCS gene of *Pasteurella multocida*. Particularly preferred is the KfoC protein (K4CP). The chondroitin synthase may be used in one kind or in a combination of two kinds or more.

Examples of the chondroitin synthase include culture of microorganisms that produces a chondroitin synthase, culture supernatant separated from the culture, microbial cells separated from the culture, or treated products of the microbial cells, or the chondroitin synthase separated from these. Accordingly, the chondroitin synthase may or may not contain components other than the chondroitin synthase. Moreover, the chondroitin synthase may be purified to the desired extent. The microorganism that produces a chondroitin synthase may be a microorganism that inherently produces a chondroitin synthase, or may be a microorganism that has been modified to produce a chondroitin synthase. The microorganism that produces a chondroitin synthase may be obtained by, for example, expressibly transforming a microorganism with a gene that encodes a chondroitin synthase. Introduction of a gene may be achieved by, for example, introducing a vector carrying the gene into a microorganism, or introducing the gene onto a chromosome of a microorganism.

The gene that encodes a chondroitin synthase is not limited to a known gene exemplified above, and may be, for example, a variant of the gene, as long as the gene encodes a protein that maintain original function. For a variant of a gene that encodes the chondroitin synthase, reference may be made mutatis mutandis to the foregoing descriptions concerning a variant of the gene used to modify a microorganism such as in imparting chondroitin-producing capability.

The "enzymatically synthesized chondroitin" may be synthesized by, for example, bringing the chondroitin synthase exemplified above into coexistence with a GlcUA donor, a GalNAc donor, and a sugar acceptor in a suitable reaction system. The reaction conditions are not particularly limited, as long as chondroitin is synthesized. The reaction conditions may be appropriately set according to conditions such as the source and the embodiment of the chondroitin synthase and the desired degree of polymerization of chondroitin. For details of reaction conditions, see, for example, the descriptions in Patent Document 8 or 9.

As used herein, "GlcUA donor" refers to a molecule that donates a GlcUA residue in chondroitin synthesis reaction by a chondroitin synthase. The type of the GlcUA donor is not particularly limited, as long as it can be used for chondroitin synthesis reaction. Examples of the GlcUA donor include GlcUA nucleotides. Examples of the GlcUA nucleotides include UDP-GlcUA (uridine 5'-diphospho-glucuronic acid). The GlcUA donor used may be a commercially available product, or may be one obtained by being appropriately produced. The GlcUA donor may be synthesized by using, for example, known techniques.

As used herein, "GalNAc donor" refers to a molecule that donates a GalNAc residue in chondroitin synthesis reaction by a chondroitin synthase. The type of the GalNAc donor is not particularly limited, as long as it can be used for chondroitin synthesis reaction. Examples of the GalNAc donor include GalNAc nucleotides. Examples of the GalNAc nucleotides include UDP-GalNAc (uridine 5'-diphospho-N-acetylgalactosamine). The GalNAc donor used may be a commercially available product, or may be one obtained by being appropriately produced. The GalNAc donor may be synthesized by using, for example, known techniques. UDP-GalNAc may be obtained through, for example, conversion of UDP-GlcNAc (uridine 5'-diphospho-N-acetylglucosamine) by the effect of UDP-Glc-4-epimerase. Moreover, UDP-GlcUA may be obtained through, for example, conversion of UDP-Glc (uridine 5'-diphospho-glucose) by the effect of UDP-Glc dehydrogenase. Accordingly, UDP-GlcNAc and/or UDP-Glc can be used as a GalNAc donor and/or a GlcUA donor for chondroitin synthesis by using a UDP-Glc-4-epimerase and/or a UDP-Glc dehydrogenase. Examples of the UDP-Glc-4-epimerase include the KfoA protein encoded by the kfoA gene. Examples of the UDP-Glc dehydrogenase include the KfoF protein encoded by the kfoF gene. Examples of the kfoA and kfoF genes include the kfoA and kfoF genes derived from *Escherichia coli* K4 strain.

As used herein, the "sugar acceptor" refers to a glycan (acceptor), wherein the elongation of the chondroitin chain takes place upon attachment of a GlcUA residue or a GalNAc residue to the non-reducing end of the acceptor in chondroitin synthesis reaction by a chondroitin synthase.

Examples of the "sugar acceptor" include the glycan represented by the following general formula (I) or (II).

$$\text{GlcUA-R}_1 \tag{I}$$

$$\text{GalNAc-R}_2 \tag{II}$$

(wherein $R_1$ and $R_2$ each represent an arbitrarily group.)

Examples of $R_1$ and $R_2$ include a hydroxyl group, or a glycan consisting of one or more residues. When $R_1$ and $R_2$ are each a glycan, "-" in the formula represents a glycoside bond. Examples of the glycan include a chondroitin chain, a heparosan chain, and a hyaluronic acid chain. Examples of the chondroitin chain include chondroitin obtained through desulfation of chondroitin sulfate and chondroitin derived from a microorganism. Moreover, the glycan also may be a derivative of these glycans. As used herein, the "derivative of glycan" refers to a glycan involving introduction, substitution, and/or removal of a constituent element such as an atom, a functional group, and a compound. Examples of the derivative of glycan include a sulfated glycan, and a glycan into which an arbitrarily sugar has been added. Specifically, the sugar acceptor moiety of the enzymatically synthesized chondroitin may have a structure corresponding to the chondroitin of the present invention or a structure that does not correspond to the chondroitin of the present invention.

In general formula (I), the GlcUA residue at the non-reducing end is preferably a β structure. In general formula (I), when $R_1$ contains a sugar residue such as GlcNAc and GalNAc, and the GlcUA residue at the non-reducing end is bound to the sugar residue of $R_1$, the bond is preferably a β-1,3-glycoside bond, or a β-1,4-glycoside bond.

In general formula (II), the GalNAc residue at the non-reducing end is preferably a β structure. In general formula (II), when $R_2$ contains a sugar residue such as GlcUA, and the GalNAc residue at the non-reducing end is bound to the sugar residue of $R_2$, the bond is preferably a β-1,4-glycoside bond.

The number of residues of the glycan in the sugar acceptor is not particularly limited, as long as the chondroitin can be synthesized. The number of residues of the glycan in the sugar acceptor may be, for example, 1 or more, 2 or more, 3 or more, 4 or more, 5 or more, 6 or more, 7 or more, 8 or more, 9 or more, or 10 or more, and is preferably 6 or more. The number of residues of the glycan in the sugar acceptor may be, for example, 50 or less, 40 or less, 30 or less, or 20 or less.

The sugar acceptor is preferably a chondroitin chain. The chondroitin chain is preferably the chondroitin of the present invention. Examples of the chondroitin of the present invention include chondroitin derived from a microorganism. Specifically, chondroitin chain with 6 or more residues, for example, can be preferably used as the sugar acceptor.

The sugar acceptor may be a commercially available product, or may be one obtained by being appropriately produced. The sugar acceptor may be prepared using, for example, known techniques.

Moreover, the reaction system may contain a surfactant. Furthermore, the reaction system may contain an organic solvent. Examples of the surfactant and the organic solvent include the surfactants or the organic solvents described in Patent Document 9.

The reaction temperature may be, for example, 10 to 50° C., 20 to 40° C., or 25 to 37° C. The reaction time may be, for example, 1 hour to 10 days, 10 to 30 hours, or 15 to 24 hours.

The enzymatically synthesized chondroitin is synthesized by a reaction performed in the manner described above. The enzymatically synthesized chondroitin may be isolated and purified in the same manner as for the microorganism-derived chondroitin.

The "enzymatically synthesized chondroitin" obtained in the manner described above is chondroitin produced in the same manner as by a reaction that a microorganism having chondroitin-producing capability carry out inside the cell, except that the reaction is reproduced by using any other method of culturing of microorganisms, for example, in vitro or in a cell-free system. That is, the "enzymatically synthesized chondroitin" is chondroitin produced by substantially the same reaction as the reaction that is carried out for producing the "microorganism-derived chondroitin". Therefore, both of them are chondroitin having essentially the same qualities of retention in blood and the like.

[2] Increasing Agent of the Present Invention

The increasing agent of the present invention is an agent for increasing protein retention in blood, the agent containing the chondroitin of the present invention as an active ingredient. The increasing agent of the present invention may contain, as an active ingredient, either microorganism-derived chondroitin or enzymatically synthesized chondroitin, or both of them. Moreover, the increasing agent of the present invention may consist of the chondroitin of the present invention, or may contain other components. The "other components" are not particularly limited, as long as they are acceptable regarding mode of use of the increasing agent of the present invention. Examples of the "other components" include, for example, components that are not detrimental to the effects of the increasing agent of the present invention and pharmacologically acceptable.

The increasing agent of the present invention may be prepared in, for example, any dosage form. The dosage form may be appropriately selected according to conditions such as mode of use of the increasing agent of the present invention. The increasing agent of the present invention may be prepared using known techniques.

The concentration of the chondroitin of the present invention in the increasing agent of the present invention is not particularly limited, as long as protein retention in blood can be increased by the increasing agent of the present invention. The concentration of the chondroitin of the present invention in the increasing agent of the present invention may be appropriately set according to such conditions as the dosage form of the increasing agent of the present invention, the type of a protein of interest, and the desired levels of retention in blood. The concentration of the chondroitin of the present invention in the increasing agent of the present invention may be, for example, 0.001 to 100% (w/w).

The increasing agent of the present invention is used so that a conjugate of the chondroitin of the present invention, which is the active ingredient in the increasing agent of the present invention, and a protein for which the retention in blood needs to be increased is formed. The increasing agent of the present invention may be used for increasing protein retention in blood, for example, either directly, or after being appropriately diluted, dispersed, or dissolved in a pharmacologically acceptable solvent such as water, physiological saline, and buffer. Such a diluted, dispersed, or dissolved form also falls within the scope of the increasing agent of the present invention.

A protein to which the increasing agent of the present invention is applied is not particularly limited, as long as it is a protein for which increasing of retention in blood is desired. The protein may be a monomeric protein or a multimeric protein. Here, the "protein" as used herein includes forms referred to as peptides, oligopeptides, or polypeptides. Examples of the protein include a protein used as a pharmaceutical (such as asparaginase, interferons, and growth hormone). Other examples of the protein include proteins used for reagents or animal testing (such as ovalbumin).

The method for forming a conjugate of the chondroitin of the present invention and a protein is not particularly limited, as long as a conjugate is formed upon contacting each other. As the method for forming a conjugate of the chondroitin of the present invention and a protein, for example, a known method for forming a conjugate of a glycosaminoglycan and a protein can be used.

The bonding mode of the two components in the conjugate is not particularly limited, as long as the conjugate is maintained. The bonding mode of the two components in the conjugate is preferably covalent linkage, for stability of the resulting conjugate. As the method for covalently linking the chondroitin of the present invention and a protein, for example, a known method for covalently linking a glycosaminoglycan and a protein can be used. Examples of such a method include the methods described in Patent Documents 1, 3, and 4.

Specifically, the covalent linkage between the chondroitin of the present invention and a protein may be achieved by, for example, introducing an aldehyde group to the chondroitin of the present invention, followed by allowing the aldehyde group to react with an amino group of a protein side chain.

The proportions of the two components in the conjugate are not particularly limited, as long as the protein retention in blood can be increased. The proportions of the two components in the conjugate may be such that, for example, the weight ratio of the chondroitin of the present invention with respect to the protein (the weight of the chondroitin of the present invention/the weight of protein) is 0.01 to 500 or 0.05 to 200.

By forming a conjugate of the chondroitin of the present invention, which is the active ingredient in the increasing agent of the present invention, and a protein, retention of the protein in blood is increased, compared to the corresponding protein that does not form a conjugate with the chondroitin of the present invention.

[3] Conjugate of the Present Invention

The conjugate of the present invention is a conjugate of the chondroitin of the present invention and a protein.

The chondroitin of the present invention and the protein that are components of the conjugate of the present invention, the method of forming the conjugate of the present invention, the bonding mode of the chondroitin and the protein in the conjugate of the present invention, and the like, are as described above in conjunction with the "increasing agent of the present invention". Accordingly, in the conjugate of the present invention, it is also preferable, for example, that the chondroitin of the present invention and a protein form a conjugate via a covalent linkage.

A protein in the conjugate of the present invention has increased retention in blood, compared to the corresponding protein that does not form a conjugate with the chondroitin of the present invention.

[4] Composition of the Present Invention

The composition of the present invention is a pharmaceutical composition containing the conjugate of the present invention. The conjugate of the present invention is as described above. Here, since the composition of the present invention is a pharmaceutical composition, preferred examples of the protein as a constituent component of the conjugate of the present invention contained in the composition of the present invention include a protein used as a pharmaceutical such as described above (such as asparaginase, interferons, and growth hormone).

The composition of the present invention may consist of the conjugate of the present invention, or may contain other components. The "other components" are not particularly limited, as long as they are acceptable regarding mode of use of the composition of the present invention. Examples of the "other components" include components that are not detrimental to the effects of the composition of the present invention and pharmacologically acceptable.

The composition of the present invention may be prepared in, for example, any dosage form. The dosage form may be appropriately selected according to conditions such as mode of use of the composition of the present invention. For example, when the composition of the present invention is used for administration into the blood (such as administration into the blood vessels (arteries or veins)) or subcutaneous administration, the composition of the present invention may be provided in the form of an injection (such as a solution form and a dry form used by being dissolved at the time of use). The composition of the present invention may be prepared using known techniques.

The concentration of the conjugate of the present invention in the composition of the present invention is not particularly limited, as long as the desired effect is achieved by the administration of the composition of the present invention. The concentration of the conjugate of the present invention in the composition of the present invention may be appropriately set according to such conditions as the dosage form of the composition of the present invention, the type of a protein contained in the composition of the present invention, and the intended purpose of the administration of the composition of the present invention. The concentration of the conjugate of the present invention in the composition of the present invention may be, for example, 0.001 to 100% (w/w).

The composition of the present invention may be administered as a pharmaceutical composition to a target in medical procedures such as prevention and treatment of a disease. The target of administration is not particularly limited, as long as it is an animal in need of medical procedures such as prevention and treatment of a disease. The target of administration is, for example, preferably a mammal, more preferably a human.

The method for administering the composition of the present invention may be appropriately set according to such conditions as the dosage form of the composition of the present invention, the type of the protein contained in the composition of the present invention, and the intended purpose of the administration of the composition of the present invention. For example, the composition of the present invention may be administered by using a method commonly used when the protein contained in the composition of the present invention is used as a pharmaceutical.

Specific examples of the administration method include, but are not limited to, administration into the blood (such as administration into the blood vessels (arteries or veins)) and subcutaneous administration. The composition of the present invention may be administered to a target, for example, either directly, or after being appropriately diluted, dispersed, or dissolved in a pharmacologically acceptable solvent such as water, physiological saline, and buffer. Such a diluted, dispersed, or dissolved form also falls within the scope of the composition of the present invention.

A protein in the conjugate of the present invention contained in the composition of the present invention has increased retention in blood, compared to the corresponding protein that does not form a conjugate with the chondroitin of the present invention.

[5] Preparation of the Present Invention

The preparation of the present invention is a protein preparation having increased retention in blood and containing the conjugate of the present invention. The conjugate of the present invention is as described above. Here, the preparation of the present invention is a concept that encompasses not only pharmaceutical preparations for animals such as human, but also preparations for reagents and animal testing etc. Accordingly, preferred examples of the protein as a constituent component of the conjugate of the present invention contained in the preparation of the present invention include a protein used as a pharmaceutical such as above (such as asparaginase, interferons, and growth hormone), and a protein used for reagents and animal testing such as above (such as ovalbumin).

For details of the preparation of the present invention, reference may be made mutatis mutandis to the above descriptions of the composition of the present invention.

A protein in the conjugate of the present invention contained in the preparation of the present invention has increased retention in blood, compared to the corresponding protein that does not form a conjugate with the chondroitin of the present invention.

[6] Increasing Method of the Present Invention

The increasing method of the present invention is a method for increasing protein retention in blood, the method comprising the step of forming a conjugate of the chondroitin of the present invention and a protein. In other words, the increasing method of the present invention is a method for producing a protein having increased retention in blood, the method comprising the step of forming a conjugate of the chondroitin of the present invention and a protein.

The chondroitin of the present invention, the protein, the method for forming a conjugate, the bonding mode of the two molecules in the conjugate, and the like, are as described above in conjunction with the increasing agent of the present invention. Accordingly, in the increasing method of the present invention, it is also preferable, for example, that the chondroitin of the present invention and a protein form a conjugate via a covalent linkage.

The increasing method of the present invention can increase protein retention in blood, compared to the corresponding protein that does not form a conjugate with the chondroitin of the present invention.

As used herein, "increasing retention in blood", and other similar terms and phrases are intended to be inclusive of ideas such as imparting retention in blood, ameliorating retention in blood, improving retention in blood, imparting persistence in blood, increasing persistence in blood, ameliorating persistence in blood, improving persistence in blood, and maintaining protein activity in blood.

Moreover, the present invention encompasses a method for producing the conjugate of the present invention, a method for producing the composition of the present invention, and a method for producing the preparation of the present invention, the methods comprising the step of forming a conjugate of the chondroitin of the present invention and a protein. For details of these producing methods, reference may be made mutatis mutandis to the above descriptions of the increasing agent of the present invention, the conjugate of the present invention, the composition of the present invention, and the preparation of the present invention.

EXAMPLES

The present invention is described below in greater detail by way of examples. However, the technical scope of the present invention is not limited by the following examples.

In the examples below, "molecular weight" means a weight-average molecular weight as measured by gel filtration chromatography.

<Example 1> Production of the Conjugate, Composition, and Preparation of the Present Invention (1) Production of Microorganism-Derived Chondroitin Microorganism-derived chondroitin was produced by using the following procedures according to a known method.

First, *Escherichia coli* K-12 W3110 strain (ATCC 27325) was transformed with four copies each of the kfoA, kfoB, kfoC, kfoF, and kfoG genes derived from *Escherichia coli* K4 strain, one copy each of the kpsF, kpsE, kpsD, kpsU, kpsC, kpsS, kpsM, and kpsT genes derived from *Escherichia coli* K4 strain, and one copy of the xylS gene derived from *Pseudomonas putida* to construct an *Escherichia coli* K-12 MSC702 strain having chondroitin-producing capability. The procedures were performed according to the method described in Patent Document 7.

NZ amine HD (160 g), Tastone 154 (4 g), $MgSO_4 \cdot 7H_2O$ (8 g), $Na_2SO_4$ (24 g), sodium citrate (2.4 g), $CaCl_2 \cdot 2H_2O$ (296 mg), and Dow 1520 US antifoam (0.8 mL) were dissolved in deionized water to prepare 6-L solution. After autoclave, glycerol (48 g), $KH_2PO_4$ (48 g), thiamine HCl (320 μg), and 24 mL of trace metal solution (containing 27 g/L of $FeCl_3 \cdot 6H_2O$, 1.3 g/L of $ZnCl_2$, 2 g/L of $CoCl_2 \cdot 6H_2O$, 2 g/L of $Na_2MoO_4 \cdot 6H_2O$, 2.5 g/L of $CaCl_2 \cdot 2H_2O$, 3.3 g/L of $MnCl_2 \cdot 4H_2O$, 0.5 g/L of $H_3BO_3$, and 33 g/L of citric acid) were aseptically added to the solution to prepare a medium.

The medium was inoculated with a 50-mL preculture of the MSC702 strain (OD600=9.0), followed by culturing. After 4 hours of culturing, m-toluic acid was added to make the final concentration 2 mM, and the cells were further cultured for 82 hours. During culture, glycerol was added as a carbon source to maintain its concentration of less than 1 g/L in the culture medium. In addition, ammonium hydroxide (ammonia water) was also added as a nitrogen source during culture to maintain its concentration of less than 100 mg/L in the culture medium. Other main culture conditions are as follows.
Temperature: 29.8 to 30.2° C.
pH: 7.1 to 7.3
Stirring: 150 to 480 cps
Dissolved oxygen: 50%
Airflow: 3.4 to 6.4 L/min
Oxygen flow: 0 to 3.1 L/min At the end of culture, the total liquid amount was 8.4 L, and the OD600 was 69. The culture medium was autoclaved and centrifuged, following the supernatant was collected. The chondroitin concentration in the culture supernatant was 8.3 g/L.

One liter of deionized water was added to 1 L of the culture supernatant (chondroitin content of 8.3 g), and the solution was centrifuged, followed by collecting the supernatant. Ethanol was then added in 4 times the volume of the supernatant, following the precipitated crude chondroitin fraction was collected. The collected crude chondroitin fraction was dissolved in 250 mL of deionized water and centrifuged, followed by collecting the supernatant. The supernatant was diluted with deionized water until the electric conductivity became 5 mS/cm or less.

The diluted solution was applied to a DEAE sepharose (GE healthcare) column (500 mL) equilibrated with deionized water. The column was washed first with 1 L of deionized water, and then with 1 L of 100 mM sodium chloride aqueous solution, following the chondroitin was eluted with 2.5 L of 300 mM sodium chloride aqueous solution. The eluate was fractionated, and the chondroitin content in each fraction was quantified using the carbazole-sulfuric acid method (Bitter T, Muir H M., Anal Biochem. 1962 October; 4: 330-4.). Fractions containing the chondroitin were combined (1.6 L), followed by concentrating to 200 mL under reduced pressure. Ethanol was added in 4 times the volume of the concentrated solution, following the chondroitin was collected as the precipitate.

The precipitate was dissolved in 200 mL of alkaline aqueous solution (pH of 10 or more), following the liquid temperature was brought to 40° C. Alkali protease (5 g; Esperase®, Novozymes) was then added to the solution, following enzymatic reaction was allowed overnight at 40° C. After neutralizing the reacted solution, ethanol was added in 4 times the volume of the solution, following the chondroitin was collected as the precipitate. The precipitate was dissolved in deionized water to make the electric conductivity 5 mS/cm or less, following the solution was applied to a DEAE sepharose (GE healthcare) column (500 mL). The column was washed with 1 L of 100 mM sodium chloride aqueous solution, following the chondroitin was eluted with a gradient of 100 mM to 500 mM sodium chloride aqueous solution.

The eluate was fractionated, and the chondroitin content in each fraction was quantified using the carbazole-sulfuric acid method. A fraction containing chondroitin (a fraction eluted with the sodium chloride aqueous solution in the vicinity of 170 mM) was then collected. The fraction was concentrated under reduced pressure, following ethanol was added in 2 times the volume of the solution to thereby obtain the purified chondroitin as the precipitate. The purified chondroitin was dissolved in deionized water and neutralized to pH 7, followed by freeze-drying. The freeze-dried chondroitin (purified product) had a weight of 4.2 g.

Before conducting the tests described in the Examples below, the microorganism-derived chondroitin (purified product) obtained above was adjusted as follows to make its molecular weight as close as possible to the molecular weights of commonly used chondroitin (chondroitin obtained through desulfation of chondroitin sulfate) and various glycosaminoglycans.

The microorganism-derived chondroitin (purified product) obtained above was dissolved in distilled water to make the final concentration 1 g/L. Hydrochloric acid was added to the solution to make the final concentration 0.5 M, following the mixture was maintained at 60° C. The solution was neutralized after 30 minutes from the start of the reaction, and thereby the reaction was quenched. The reacted solution was dialyzed against 10 L of deionized water with a dialysis membrane with a molecular weight cut-off (MWCO) of 1 K, followed by freeze-drying. This operation was repeated twice, and microorganism-derived chondroitin (freeze dried product) with molecular weights of $48\times10^3$ and $46\times10^3$ were obtained.

Moreover, by using the same procedures, microorganism-derived chondroitin (freeze dried products) with molecular weights of $7\times10^3$, and $5\times10^3$ were obtained. Specifically, the reaction was quenched after 4.5 hours and 5 hours from the start of the reaction, following the product was dialyzed and freeze dried.

Hereafter, these microorganism-derived chondroitin also will be collectively referred to as "rCH". Moreover, the rCH with a molecular weight of $48\times10^3$, the rCH with a molecular weight of $46\times10^3$, the rCH with a molecular weight of $7\times10^3$, and the rCH with a molecular weight of $5\times10^3$ will be referred to as "rCH48", "rCH46", "rCH7", and "rCH5", with the abbreviations, respectively.

(2) Obtaining of Proteins

The following commercially available proteins were used.
L-Asparaginase (hereinafter, "Asp"; Kyowa Hakko Kirin Co., Ltd.; trade name Leunase)
Interferon β2b (hereinafter, "IFN"; PROSPEC)
Ovalbumin (hereinafter, "OVA"; Sigma Aldrich)
Growth hormone (hereinafter, "GH"; (Sand; trade name Somatropin BS, s.c.)

(3) Production of Conjugates of Microorganism-Derived Chondroitin and Proteins (Asp, IFN, OVA) (Formation of Covalent Linkage)

Firstly, for reaction with amino groups of a protein, an aldehyde group was introduced to the microorganism-derived chondroitin, as follows.

The microorganism-derived chondroitin was dissolved in water to make the concentration 50 mg/mL. After adding ½ volume of 2 mg/mL sodium borohydride aqueous solution, the mixture was allowed to react overnight at room temperature. Sodium acetate was then added to the solution to make its concentration 3% (w/v), following ethanol was added in 2 times the volume of the solution to thereby obtain a precipitate. The precipitate was dissolved in 5 mL of phosphate buffer (pH 7) and 5 molar equivalent of sodium periodate was added, followed by allowing the reaction to proceed at 4° C. for 1 hour. A 1/30 volume of ethylene glycol was added to the solution and the reaction was allowed to proceed at 4° C. for 1 hour again. Sodium acetate was then added to the solution to make its concentration 3% (w/v), following ethanol was added in 2 times the volume of the solution to thereby obtain a precipitate. The precipitate was dissolved in water and dialyzed, followed by freeze drying, to thereby obtain microorganism-derived chondroitin (freeze dried product) with the introduced aldehyde group.

Next, the microorganism-derived chondroitin with the introduced aldehyde group was covalently bonded to the protein by using trimethylamine borane as a reducing agent.

Specifically, the protein (1 mg) and the microorganism-derived chondroitin with the introduced aldehyde group (15 mg) were dissolved in 1 mL of 0.2 M potassium phosphate buffer (pH 9). Thereafter, 1 mg of trimethylamine borane was added to the solution, following the reaction was allowed to proceed at room temperature for 24 hours. Then, the operation, in that 1 mg of trimethylamine borane was added to the solution and the reaction was allowed to proceed at room temperature for 24 hours, was repeated three times. The unreactant in the reacted solution was removed by hydrophobic column chromatography and the eluate was collected, followed by desalting and concentrating the eluate by ultrafiltration, to thereby obtain a fraction containing a conjugate of the microorganism-derived chondroitin and the protein.

Hereafter, the conjugate of rCH and Asp, the conjugate of rCH and IFN, and the conjugate of rCH and OVA produced in the manner described above will be referred to with the abbreviations "rCH-Asp", "rCH-IFN", and "rCH-OVA", respectively.

(4) Production of a conjugate of Microorganism-Derived Chondroitin and a Protein (GH) (Formation of Covalent Linkage)

Firstly, in order to form covalent linkages with amino groups of a protein, an aldehyde group was introduced to the microorganism-derived chondroitin, as follows.

The microorganism-derived chondroitin was dissolved in phosphate buffer (pH 7) to make the concentration 20 mg/mL and the solution was mixed with 2 molar equivalent of sodium periodate, followed by allowing the reaction to proceed at 4° C. for 24 hours. 2 molar equivalent of cis 1,2-cyclohexanediol was mixed with the solution and the reaction was allowed to proceed at 4° C. for 1 hour, followed by dialyzing against water and freeze drying, to thereby obtain microorganism-derived chondroitin with the introduced aldehyde group.

Next, the microorganism-derived chondroitin with the introduced aldehyde group was covalently bonded to the protein through reductive amination, by using sodium cyanoborohydride as a reducing agent.

Specifically, the protein (0.5 mg) and the microorganism-derived chondroitin with the introduced aldehyde group (18.0 mg) were dissolved in 1 mL of 0.1 M bicin (N,N-bis (2-hydroxyethyl)glycine) buffer (pH 9) containing 0.2% Pluronic F68. 2.8 mg of sodium cyanoborohydride was mixed with the solution, following the reaction was allowed to proceed at room temperature for 24 hours. The unreactant in the reacted solution was removed by hydrophobic column chromatography and the eluate was collected, followed by desalting and concentrating the eluate by ultrafiltration, to thereby obtain a fraction containing a conjugate of the microorganism-derived chondroitin and the protein.

Hereafter, the conjugate of rCH and GH produced in the manner described above will be referred to as "rCH-GH" with the abbreviation.

(5) Production of Pharmaceutical Composition and Preparation

The rCH-Asp, rCH-IFN, rCH-OVA produced in section (3) above and the rCH-GH produced in section (4) above were each diluted with physiological saline to the desired concentration, to thereby prepare a pharmaceutical composition. Moreover, the pharmaceutical compositions were charged into injection syringes, to thereby make them preparations for intravascular administration or subcutaneous administration, and they were used in below described Example 2.

<Reference Example> Production of Comparative Product (1) Various Glycosaminoglycans As comparative products of rCH, the following hyaluronic acid (products of Seikagaku Corporation or Lifecore Biomedical), various sulfated glycosaminoglycans (products of Seikagaku Corporation), and heparosan were used.

The molecular weights of these products were adjusted by using the method described in section (1) of Example 1.

Chondroitin sulfate A (hereinafter, "CSA"; derived from whale cartilage; molecular weight $6 \times 10^3$)

Chondroitin sulfate C (hereinafter, "CSC"; derived from shark cartilage; molecular weights $6 \times 10^3$, $38 \times 10^3$)

Chondroitin sulfate E (hereinafter, "CSE"; derived from squid cartilage; molecular weight $9 \times 10^3$)

Dermatan sulfate (hereinafter, "DS"; derived from rooster crest; molecular weight $5 \times 10^3$)

Hyaluronan (hereinafter, "HA"; derived from rooster crest; molecular weights $5 \times 10^3$, $47 \times 10^3$; Product of Seikagaku Corporation)

Hyaluronan (hereinafter, "HA"; derived from microorganism; molecular weight $66 \times 10^3$; Product of Lifecore Biomedical)

Heparosan (hereinafter, "HPN"; derived from *Escherichia coli* K5 strain; molecular weights $5 \times 10^3$, $36 \times 10^3$)

Heparin (hereinafter, "HP"; derived from pig intestine; molecular weight $9 \times 10^3$)

Heparan sulfate (hereinafter, "HS"; derived from pig kidney; molecular weight $14 \times 10^3$)

hereafter, as with the case of rCH, the various glycosaminoglycans will be abbreviated to, for example, "CSC6", "CSC38", and "HPN36" for the CSC with a molecular weight of $6 \times 10^3$, the CSC with a molecular weight of $38 \times 10^3$, and the HPN with a molecular weight of $36 \times 10^3$, respectively.

(2) Production of Heparosan (HPN)

HPN was produced by culturing *Escherichia coli* K5 strain (Serotype O10:K5(L):H4, ATCC 23506) and purifying the culture supernatant, according to the methods described in known document (JP-A-2004-018840).

(3) Production of Commonly Used Chondroitin

Commonly used chondroitin (chondroitin obtained through desulfation of chondroitin sulfate) was produced by using a common industrial method for chondroitin production, as follows.

Chondroitin sulfate was desulfated according to the method described in J. Am. Chem. Soc., 1957, 79 (1), pp 152-153.

Acetyl chloride (7 mL) was dropped on methanol (93 mL) to prepare hydrochloric acid-methanol solution. To the solution was then added 10 g of CSC (derived from shark cartilage; unadjusted molecular weight; Product of Seikagaku Corporation). The suspension was stirred at room temperature for 20 hours and a 30-mL aliquot was taken out of the solution, followed by centrifuging and collecting the precipitate.

The collected precipitate was dissolved in 30 mL of distilled water, followed by adjusting pH to around neutral. The solution was then dialyzed overnight against running water by using a dialysis membrane with a MWCO of 12000 to 14000, followed by freeze drying.

The freeze dried product (1 g) was dissolved in 50 mL of 0.1 M sodium hydroxide aqueous solution, following the solution was stirred overnight at room temperature. Then, the solution was neutralized, following the solution was dialyzed overnight against running water by using a dialysis membrane with a MWCO of 12000 to 14000. The dialyzed solution was freeze dried to obtain commonly used chondroitin (freeze dried product). The chondroitin had a molecular weight of $7 \times 10^3$.

Hereafter, chondroitin obtained through desulfation of chondroitin sulfate also will be referred to as "dCH". Moreover, the dCH with a molecular weight of $7 \times 10^3$ will be referred to as "dCH7", with the abbreviation.

(4) Production of Conjugates of Protein and Various Glycosaminoglycans or dCH

Conjugates of Asp, IFN, or OVA and glycosaminoglycans or dCH were produced by using the method described in section (3) of Example 1.

Hereafter, as with the case of rCH, the conjugates containing various glycosaminoglycans will be abbreviated to, for example, "CSA-Asp" and "dCH-OVA" for the conjugate of CSA and Asp and the conjugate of dCH and OVA, respectively.

These conjugates were used to form preparations by using the same method as described in section (5) of Example 1, and the preparations were used in Example 2.

<Example 2> Measurement of Retention in Blood of Conjugate of Glycosaminoglycan and Protein (1) Test Method 1 (Asp)

The following test was conducted for a test sample containing "Asp" as a protein (a conjugate containing Asp, or the Asp itself).

The test sample was injected into the tail vein of male ICR mice (three per group) in a dose of 1 mg protein/kg body weight.

Blood was collected from the mice at hour 8, 24, 48, 72, 96, and 120 after administration, followed by centrifugation to obtain plasma.

Asp retention in blood was measured by using Asp activity in the plasma as an index. The Asp activity in the plasma was calculated by using, as an index, the amount of ammonia generated when Asp transformed asparagine to aspartic acid. Specifically, 10 μL of the plasma diluted 10 to 40 times was added to 0.1 M Tris buffer (pH 8) containing 200 μL of 2.55 mg/mL asparagine, followed by incubation at 37° C. for 30 minutes. 10 μL of trichloroacetic acid was then added to the reacted solution, followed by centrifugation. After centrifugation, 10 μL of the supernatant was mixed with Nessler's reagent to allow reaction with the ammonia contained in the supernatant. The absorbance at 450 nm was then measured by using the Well Reader SK603 (Seikagaku Corporation).

(2) Test Method 2 (IFN)

The following test was conducted for a test sample containing "IFN" as a protein (a conjugate containing IFN, or the IFN itself).

The test sample was subcutaneously injected into male ICR mice (three per group) in a dose of 0.2 mg protein/kg body weight.

Blood was collected from the mice at hour 2, 4, 8, 24, 48, 72, and 96 after administration, followed by centrifugation to obtain plasma.

IFN retention in blood was measured by using IFN activity in the plasma as an index. The IFN activity in the plasma was measured by using luminescence from luciferase activity as an index. The measurement was conducted by using the iLite Alphabeta Kit (Biomonitor Limited), and according to the method described in the kit manual. Luminescence intensity was measured by using the Multilabel Reader 2030 ARVO (PerkinElmer).

(3) Test Method 3 (OVA)

The following test was conducted for a test sample containing "OVA" as a protein (a conjugate containing OVA, or the OVA itself).

The test sample was injected into the tail vein of male ICR mice (three per group) in a dose of 0.8 mg protein/kg body weight.

Blood was collected from the mice at hour 2, 4, 8, 24, 48, 72, and 96 after administration, followed by centrifugation to obtain plasma.

OVA retention in blood was measured by using OVA concentration in the plasma as an index. The OVA concentration in the plasma was measured by using the ITEA OVA ELISA Kit (ITEA). The measurement was conducted according to the method described in the kit manual. For the generation of a standard curve, the OVA itself was used as a standard for the plasma of individuals administered with the OVA itself. For the plasma of individuals administered with the conjugate containing OVA, the OVA-containing conjugate was used as a standard. Absorbance was measured by using the Well Reader SK603 (Seikagaku Corporation).

(4) Test Method 4 (GH)

The following test was conducted for a test sample containing "GH" as a protein (a conjugate containing GH, or the GH itself).

The test sample was injected into the tail vein of male ICR mice (three per group) in a dose of 0.1 mg protein/kg body weight.

Blood was collected from the mice at hour 0.5, 2, 4, and 8 after administration for the mice administered with the GH itself, and at hour 8, 24, 48, and 72 after administration for the mice administered with the conjugate of GH and a glycosaminoglycan, followed by centrifugation to obtain plasma.

GH retention in blood was measured by using GH concentration in the plasma as an index. The GH concentration in the plasma was measured by using the hGH ELISA Kit (Roche Diagnostics). The measurement was conducted according to the method described in the kit manual. For the generation of a standard curve, the GH itself was used as a standard for the plasma of individuals administered with the GH itself. For the plasma of individuals administered with the conjugate containing GH, the GH-containing conjugate was used as a standard. Absorbance was measured by using the Well Reader SK603 (Seikagaku Corporation).

(5) Calculation of Half-Life

Half-life in blood (t½) was calculated by using the transition data of the measured Asp activity, IFN activity, OVA concentration, and GH concentration in blood. The data of three time points from the last measurement point of each individual were analyzed in a model independent analysis by using the Phoenix WinNonlin (Certara). Hereafter, half-life in blood (t½) is represented as average value±standard error (SE).

(6) Test Using rCH 1 (Comparison with Various Glycosaminoglycans)

The retention in blood of the test samples "rCH7-Asp", and the "conjugates of various glycosaminoglycans and Asp" were measured by using the test method described in section (1) above.

In the tests, the following "conjugates of glycosaminoglycans and Asp" were used to make the molecular weight of the glycan moiety as close as possible to rCH ($7 \times 10^3$).

CSA6-Asp
CSC6-Asp
CSE9-Asp
DS5-Asp
HA5-Asp
HPN5-Asp
HP9-Asp
HS14-Asp

In addition, unmodified Asp was used as a control sample. The results are presented in FIG. 1.

Figure 1:
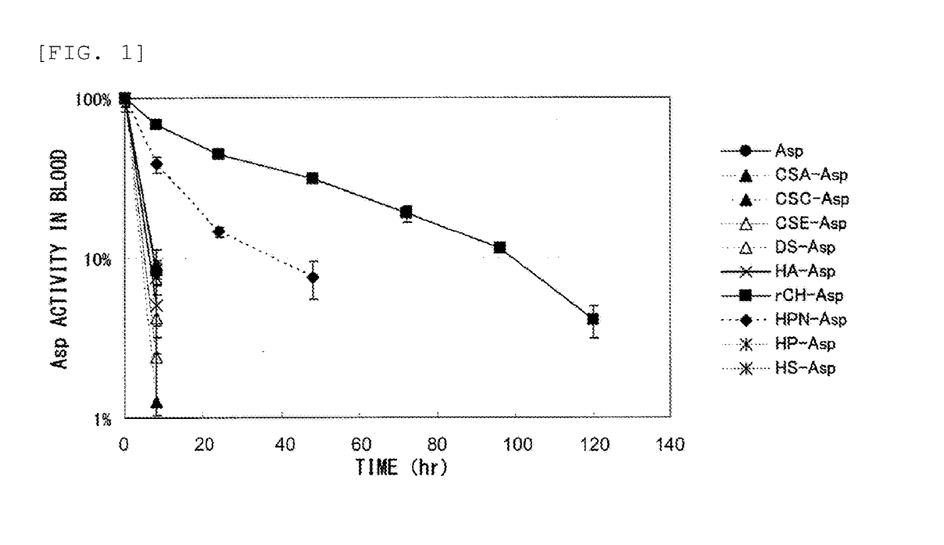
[FIG. 1] A diagram for comparing protein retention in blood, when a conjugate of a protein (asparaginase) with each of various glycosaminoglycans and chondroitin produced by a microorganism was formed.

As can be seen from FIG. 1, it was shown that the protein retention in blood was more prominently increased when rCH was used to form a protein conjugate than when other glycosaminoglycans were used.

This result is also in consistent with the difference of half-life in blood (t½) between "rCH7-Asp" and "HPN5-Asp" which had the second highest half-life in blood, as described below.

rCH7-Asp: 35.21±3.14 hours
HPN5-Asp: 9.00±0.46 hours (7) Test Using rCH 2 (Comparison with Various Glycosaminoglycans)

The retention in blood of the test samples "rCH46-IFN", and the "conjugates of various glycosaminoglycans and IFN" were measured by using the test method described in section (2) above.

In the tests, the following "conjugates of glycosaminoglycans and IFN" were used to make the molecular weight of the glycan moiety as close as possible to rCH ($46 \times 10^3$).

CSC38-IFN
HA47-IFN
HPN36-IFN

In addition, unmodified IFN was used as a control sample. The results are presented in FIG. 2.

Figure 2:
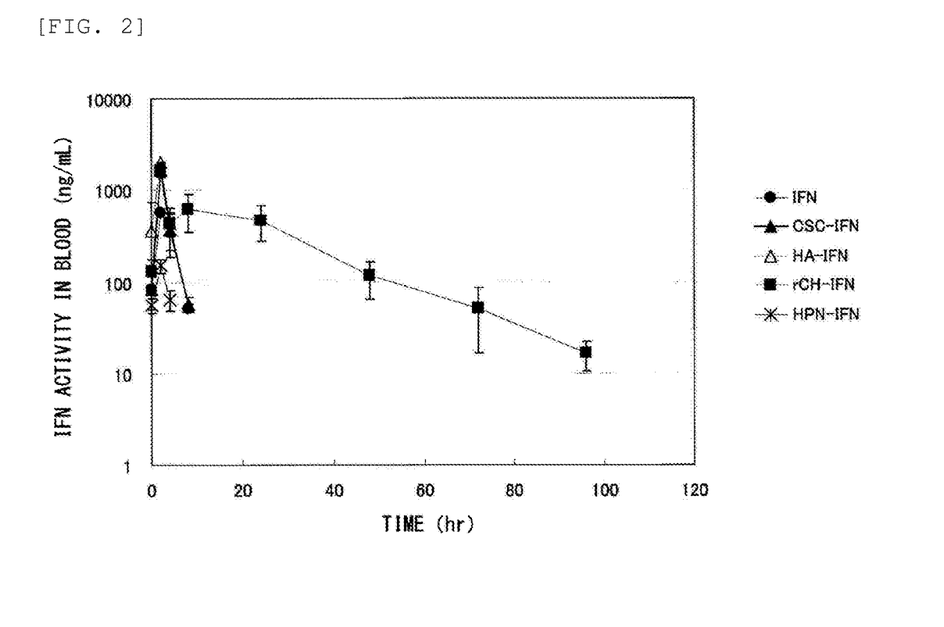
[FIG. 2] A diagram for comparing protein retention in blood, when a conjugate of a protein (interferon) with each of various glycosaminoglycans and chondroitin produced by a microorganism was formed.

As can be seen from FIG. 2, it was confirmed that the protein retention in blood was more prominently increased when rCH was used to form a protein conjugate than when other glycosaminoglycans were used.

This result is also in consistent with the differences of half-life in blood (t½) between "rCH46-IFN" and other conjugates, as described below.

rCH46-IFN: 18.22±2.56 hours
CSC38-IFN: 1.28±0.10 hours
HA47-IFN: 1.18±0.04 hours (8) Test Using rCH 3 (Comparison with dCH)

The retention in blood of the test samples "rCH5-Asp" and "dCH7-Asp" were measured by using the test method described in section (1) above. The results are presented in FIG. 3.

Figure 3:
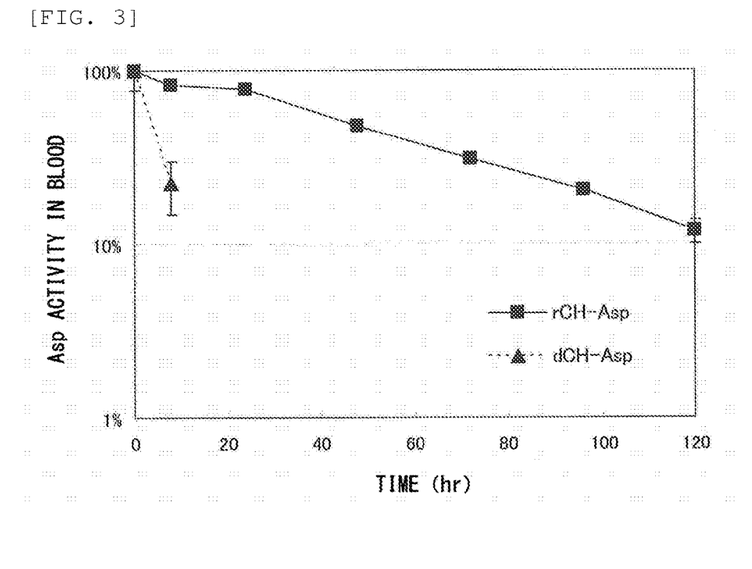
[FIG. 3] A diagram for comparing protein retention in blood, when a conjugate of a protein (asparaginase) with each of chondroitin produced by desulfation of chondroitin sulfate and chondroitin produced by a microorganism was formed.

As can be seen from FIG. 3, it was found, rather surprisingly, that the protein retention in blood was remarkably higher when rCH was used to form a protein conjugate than when dCH was used, despite that rCH and dCH were both generally called chondroitin.

(9) Test Using rCH 4 (Comparison with Various Glycosaminoglycans and dCH)

The retention in blood of the test samples "rCH5-OVA", "dCH7-OVA", and the "conjugates of various glycosaminoglycans and OVA" were measured by using the test method described in section (3) above.

In the tests, the following "conjugates of glycosaminoglycans and OVA" were used to make the molecular weight of the glycan moiety as close as possible to rCH ($5 \times 10^3$).

CSC6-OVA
HA5-OVA

In addition, unmodified OVA was used as a control sample. The results are presented in FIG. 4.

Figure 4:
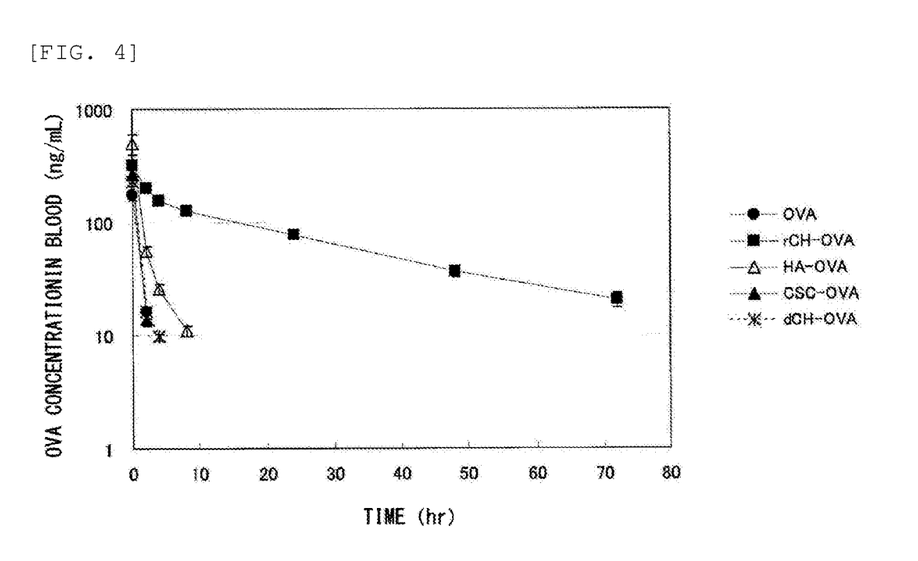
[FIG. 4] A diagram for comparing protein retention in blood, when a conjugate of a protein (ovalbumin) with each of various glycosaminoglycans, chondroitin produced by desulfation of chondroitin sulfate, and chondroitin produced by a microorganism was formed.

As can be seen from FIG. 4, it was confirmed that the protein retention in blood was more prominently increased when rCH was used to form a protein conjugate than when other glycosaminoglycans were used. Moreover, it was again confirmed that the protein retention in blood was remarkably higher when rCH was used to form a protein conjugate than when dCH was used.

This result is also in consistent with the differences of half-life in blood (t½) between "rCH5-OVA" and other conjugates, as described below.

rCH5-OVA: 24.34±2.02 hours
dCH7-OVA: 3.61±0.10 hours
CSC6-OVA: 2.60±0.05 hours
HA5-OVA: 2.64±0.05 hours (10) Test Using rCH 5

The retention in blood of the test sample "rCH7-GH" was measured by using the test method described in section (4) above.

Unmodified GH was used as a control sample. The results are presented in FIG. 5.

Figure 5:
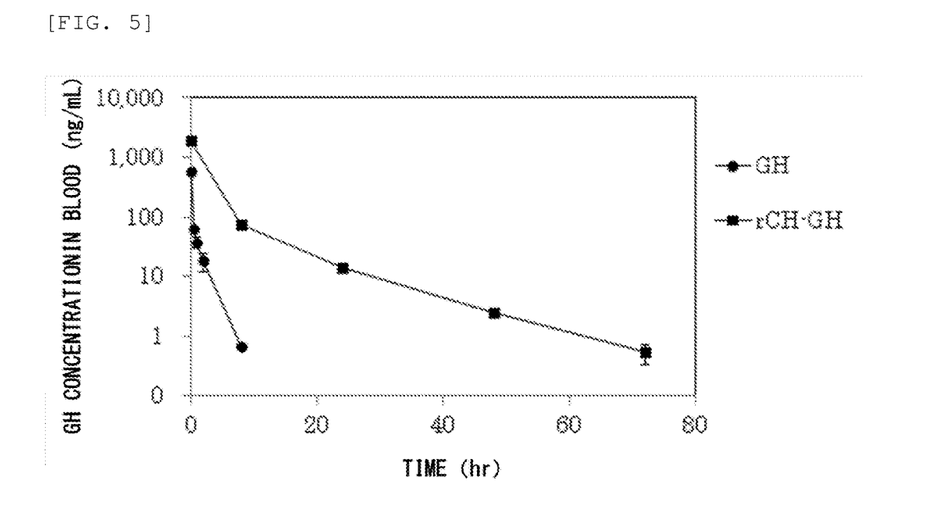
[FIG. 5] A diagram for representing protein retention in blood, when a conjugate of a protein (growth hormone) with chondroitin produced by a microorganism was formed.

As can be seen from FIG. 5, it was confirmed that the protein retention in blood could be greatly increased when rCH was used to form a protein conjugate.

This result is also in consistent with the difference of half-life in blood (t½) between "rCH7-GH" and unmodified GH, as described below.

rCH7-GH: 9.90±1.37 hours
Unmodified GH: 1.27±0.10 hours

<Example 3> Measurement of Glycosaminoglycan Retention in Blood (1) Production of Defructosylated K4 Polysaccharide Defructosylated K4 polysaccharide was produced as follows. *Escherichia coli* K4 strain (serotype O5:K4(L):H4) was cultured according to the method described in Patent Document 5. The culture supernatant was purified to obtain K4 polysaccharide (fructosylated chondroitin), following the fructose residue was removed (defructosylated) from the K4 polysaccharide by acid hydrolysis reaction in the manner described below as taught in known document (Lidholt K, Fjelstad M., J Biol Chem. 1997 Jan. 31; 272(5): 2682-7).

The K4 polysaccharide (313.9 mg) was dissolved in 30 mL of distilled water, followed by mixed with hydrochloric acid to bring the pH to 1.5. The solution was incubated at 80° C. for 30 minutes, and the fructose residues were removed by acid hydrolysis reaction. After being neutralized, the solution was dialyzed against water, followed by freeze dried to thereby obtain 196.1 mg of defructosylated K4 polysaccharide. The defructosylated K4 polysaccharide had a molecular weight of $38 \times 10^3$.

Hereafter, the defructosylated K4 polysaccharide will be referred to as "dfCH". The defructosylated K4 polysaccharide with a molecular weight of $38 \times 10^3$ will be abbreviated to "dfCH38".

(2) Measurement of Glycosaminoglycan retention in Blood

Retention in blood of the test samples "rCH48", "dfCH38", and "various glycosaminoglycans" were measured, as follows.

In the tests, the following "various glycosaminoglycans" were used as test samples, to make the molecular weight of the glycosaminoglycans as close as possible to rCH 48 ($48 \times 10^3$).

CSC38
HA66

The glycosaminoglycans were injected into the tail vein of male ICR mice (three at each time point per group) in a dose of 10 mg/kg.

Blood was collected from the heart of the mice at hour 4, 8, 24, 48, 72, and 96 after administration for the mice administered with rCH or dfCH, at hour 0.25, 0.5, 1, 2, 4, and 6 after administration for the mice administered with CSC, and at hour 1, 6, 14, 24, 48, and 72 after administration for the mice administered with HA, followed by centrifugation to obtain plasma.

The concentration of the glycosaminoglycan in plasma was measured by using HPLC post-column derivatization method, as follows.

40 μL of 0.1 M Tris buffer (pH 8.0), 25 μL of enzyme solution (containing 5 U/mL chondroitinase ABC, 0.5 U/mL chondroitinase ACII, and 0.1% BSA), and distilled water were mixed with 50 μL of plasma to make the total amount 200 μL. After incubation at 37° C. for 2 hours, the reacted solution was subjected to ultrafiltration using a spin column with a molecular weight cut-off (MWCO) of 10 K, following the filtrate was collected. The filtrate (50 μL) was passed through an anion exchange column, following the eluted sugars were detected by post-column derivatization method to measure concentration of the glycosaminoglycans in plasma.

YMC-Pack PA-G (inner diameter: 4.6 mm×length: 150 mm; Product of YMC) was used as an ion exchange column with a column temperature maintained at room temperature. Solvent A (5% ethanol) and solvent B (200 mM sodium sulfate/5% ethanol) were used as the mobile phase in the elution, which was performed in a linear gradient from 0% to 100% proportion of solvent B within the first 30 minutes of the analysis. The flow rate was set to 0.4 mL/min.

The column eluate and a derivatization reagent (containing 1% 2-cyanoacetamide and 50 mM sodium tetraborate (pH 9.0)) were mixed through a three-way joint while feeding the derivatization reagent at flow rate of 0.225 mL/min. The mixed solution was passed first through a reaction coil (inner diameter: 0.5 mm×length: 10 m) and then through a fluorescence detector. The reaction coil was used with being heated at 145° C. The fluorescence detector was used at an excitation wavelength of 346 nm and a fluorescence wavelength of 410 nm. The reaction coil and the fluorescence detector were connected to each other via a back-pressure coil.

Half-life in blood (t½) was calculated by using the transition data of the measured glycosaminoglycan concentration in plasma. The mean value data of three time points from the last measurement point were analyzed in a model independent analysis by using Phoenix WinNonlin.

Figure 6:
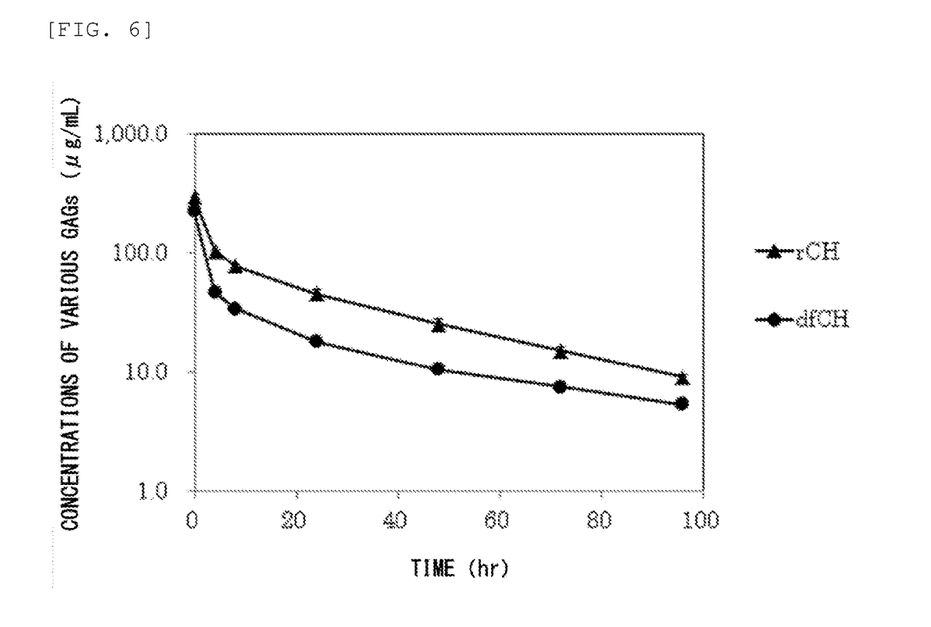
[FIG. 6] A diagram for representing retention in blood of chondroitin produced by a microorganism.

The concentration transitions of rCH and dfCH in plasma are shown in FIG. 6. As can be seen from FIG. 6, microorganism-derived chondroitin (rCH and dfCH) were both shown to have prominently long retention in blood. The patterns of concentration transitions in plasma were similar between rCH and dfCH, showing that both are chondroitin having the same quality in terms of retention in blood.

The differences of half-life in blood (t½) between chondroitin ("rCH" and "dfCH") and "other glycosaminoglycans" described below showed that rCH and dfCH had much longer retention in blood than other glycosaminoglycans.

rCH48: 32.2 h dfCH38: 38.0 h

CSC38: 0.9 h

HA66: 2.2 h

As demonstrated in sections (6) to (10) of Example 2, microorganism-derived chondroitin can exert remarkably long retention in blood when used for forming conjugates with proteins. Because rCH and dfCH themselves have remarkably long retention in blood, the increasing effect of protein retention in blood by these microorganism-derived chondroitin is considered to be due to the property of microorganism-derived chondroitin themselves, i.e. the property of the microorganism-derived chondroitin being imparted on proteins when forming conjugates with the proteins. Therefore, microorganism-derived chondroitin can be used as an agent for increasing retention in blood not only for specific proteins but for any proteins. Moreover, because, for example, rCH and dfCH have the same quality in terms of retention in blood of the glycan itself, both can be considered as chondroitin having the same quality also in terms of the increasing effect of protein retention in blood. Therefore, not only chondroitin derived from a specific microorganism, but chondroitin derived from any microorganism, can be used as an agent for increasing protein retention in blood.

INDUSTRIAL APPLICABILITY

The present invention can greatly increase protein retention in blood. Therefore, the present invention enables, for example, maintaining the effect of pharmaceutical or preparations containing a protein as an active ingredient, for extended time periods. Accordingly, the present invention is highly useful for clinical practice and/or research.

The disclosure of Japanese patent application 2013-204053 (filed Sep. 30, 2013) is hereby incorporated by reference in its entirety. All publications, patent applications, and technical specifications described herein are hereby incorporated by reference to the same extent as when these publications, patent applications, and technical specifications were specifically and individually recited as being incorporated by reference.

The invention claimed is:

1. A method for increasing retention of a protein in blood compared to a conjugate of the protein and chondroitin produced by desulfation of chondroitin sulfate, the method comprising the step of forming a conjugate of a protein and a non-sulfated chondroitin by a covalent bond, wherein said non-sulfated chondroitin is produced by a microorganism having chondroitin-producing capability and/or said non-sulfated chondroitin is enzymatically synthesized by a chondroitin synthase, and said protein conjugate has increased retention in blood compared to the corresponding conjugate of the protein and chondroitin produced by desulfation of chondroitin sulfate.

2. The method according to claim 1 further comprising introducing an aldehyde group onto the non-sulfated chondroitin.

* * * * *

UNITED STATES PATENT AND TRADEMARK OFFICE
CERTIFICATE OF CORRECTION

PATENT NO. : 10,196,625 B2
APPLICATION NO. : 15/025606
DATED : February 5, 2019
INVENTOR(S) : Yoshihiro Takatsu and Masanobu Fukushima It is certified that error appears in the above-identified patent and that said Letters Patent is hereby corrected as shown below:

In the Drawings

Sheet 2 of 3, FIG. 4, y-axis, please delete "CONCENTRATIONIN" and insert -- CONCENTRATION IN -- therefor.

Sheet 3 of 3, FIG. 5, y-axis, please delete "CONCENTRATIONIN" and insert -- CONCENTRATION IN -- therefor.

Sheet 3 of 3, FIG. 6, please delete "(μ g/mL)" and insert -- (μg/mL) -- therefor.

In the Specification

Column 4, Line 43, please delete "(→4]" and insert -- (1→] -- therefor.

Column 5, Line 20, please delete "$1 \times 10^6$," and insert -- $1 \times 10^5$, -- therefor.

Column 6, Line 20, please delete "meffloti;" and insert -- meliloti; -- therefor.

Column 7, Line 55, please delete "orf3(kfoI)," and insert -- orf3 (kfoI), -- therefor.

Column 8, Line 50, please delete "(kfoII)," and insert -- (kfoI), -- therefor.

Column 19, Line 20, please delete ""rCH46","rCH7"," and insert -- "rCH46", "rCH7", -- therefor.

Column 19, Line 25, please delete "Leunase)" and insert -- Leunase®) -- therefor.

Column 19, Line 26, please delete "β2b" and insert -- α2b -- therefor.

Signed and Sealed this
Twenty-first Day of May, 2019

Andrei Iancu
*Director of the United States Patent and Trademark Office*